(12) United States Patent
Parachur et al.

(10) Patent No.: US 11,696,900 B2
(45) Date of Patent: Jul. 11, 2023

(54) TRI-MOLECULAR COMPLEX OF NATURAL COMPOUNDS

(71) Applicants: Vivek Anand Parachur, Chennai (IN); Somashekara Nirvanashetty, Chennai (IN)

(72) Inventors: Vivek Anand Parachur, Chennai (IN); Somashekara Nirvanashetty, Chennai (IN)

(73) Assignee: OLENE LIFE SCIENCES PRIVATE LIMITED, Chennai (IN)

( * ) Notice: Subject to any disclaimer, the term of this patent is extended or adjusted under 35 U.S.C. 154(b) by 807 days.

(21) Appl. No.: 16/063,110

(22) PCT Filed: Dec. 16, 2016

(86) PCT No.: PCT/IN2016/050444
§ 371 (c)(1),
(2) Date: Jun. 15, 2018

(87) PCT Pub. No.: WO2017/103946
PCT Pub. Date: Jun. 22, 2017

(65) Prior Publication Data
US 2020/0276134 A1    Sep. 3, 2020

(30) Foreign Application Priority Data
Dec. 16, 2015   (IN) .......................... 6738/CHE/2015

(51) Int. Cl.
| | | |
|---|---|---|
| A61K 31/12 | (2006.01) | |
| A61K 31/047 | (2006.01) | |
| A61K 31/352 | (2006.01) | |
| A61K 31/4375 | (2006.01) | |
| A61K 36/185 | (2006.01) | |
| A61K 36/28 | (2006.01) | |
| A61K 36/324 | (2006.01) | |
| A61K 36/38 | (2006.01) | |
| A61K 36/48 | (2006.01) | |
| A61K 36/53 | (2006.01) | |
| A61K 36/54 | (2006.01) | |
| A61K 36/81 | (2006.01) | |
| A61K 36/88 | (2006.01) | |
| A61K 36/9066 | (2006.01) | |
| A61K 36/9068 | (2006.01) | |
| A61K 47/02 | (2006.01) | |
| A61K 47/12 | (2006.01) | |
| A61K 47/24 | (2006.01) | |

(52) U.S. Cl.
CPC ............ *A61K 31/12* (2013.01); *A61K 31/047* (2013.01); *A61K 31/352* (2013.01); *A61K 31/4375* (2013.01); *A61K 36/185* (2013.01); *A61K 36/28* (2013.01); *A61K 36/324* (2013.01); *A61K 36/38* (2013.01); *A61K 36/48* (2013.01); *A61K 36/53* (2013.01); *A61K 36/54* (2013.01); *A61K 36/81* (2013.01); *A61K 36/88* (2013.01); *A61K 36/9066* (2013.01); *A61K 36/9068* (2013.01); *A61K 47/02* (2013.01); *A61K 47/12* (2013.01); *A61K 47/24* (2013.01)

(58) Field of Classification Search
None
See application file for complete search history.

(56) References Cited

U.S. PATENT DOCUMENTS

| | | | |
|---|---|---|---|
| 2009/0131373 A1 | 5/2009 | Giori et al. | |
| 2015/0202246 A1* | 7/2015 | Bombardelli | A61P 43/00 |
| | | | 424/479 |

FOREIGN PATENT DOCUMENTS

| | | |
|---|---|---|
| CN | 1438225 A | 8/2003 |
| CN | 1657040 A | 8/2005 |
| EP | 2229940 B1 | 9/2010 |
| WO | 2007/101551 A2 | 9/2007 |
| WO | 2014135967 A1 | 9/2014 |
| WO | 2015124616 A1 | 8/2015 |

OTHER PUBLICATIONS

Melcrova et al., Scientific reports, pp. 1-12, 2016.*

* cited by examiner

*Primary Examiner* — Michael V Meller
(74) *Attorney, Agent, or Firm* — Kramer & Amado, P.C.

(57) ABSTRACT

The invention discloses a composition exhibiting enhanced bioavailability comprising tri-molecular complex of a natural compound or a natural compound containing component, a divalent or tri-valent metal ion and a phospholipid embedded in natural matrix. The composition of the invention further exhibits a sustained release profile for the natural compound or natural compound containing component. The invention further discloses a process for manufacturing the tri-molecular complex containing composition.

6 Claims, 16 Drawing Sheets

TRI-MOLECULAR COMPLEX OF NATURAL COMPOUNDS

FIELD OF INVENTION

The present invention is in field of composition for the prevention, management and treatment of human and animal diseases/disorders and for restoring health. More particularly, the invention relates to a tri-molecular complex of a natural compound demonstrating enhanced bioavailability and sustained release and process for preparation thereof.

BACKGROUND OF INVENTION

In India, knowledge of medicinal plants is very old. The medicinal properties of plants are described in Rigveda and Atharvaveda, from which Ayurveda has been developed. Most of medicines mentioned therein have been derived from plants like pepper, lily, valerian, turmeric etc.

Over the past two decades, the usage of botanical dietary supplements has steadily increased worldwide. This growing popularity has been especially notable among people in Western countries, where almost 20% of consumers report regular usage of such supplements. Various herbal drugs individually or in combination have been recommended for the treatment of variety of diseases. One of the main reasons for the recent spur in popularity of the herbal drugs is, in part, no or negligible chance of side-effects even during accidental overdosing or any cross reaction of the components.

Despite their popularity, demonstrable efficacy has remained elusive for many of these agents. The effect of any dietary compound is influenced by the active bioavailable dose rather than the dose ingested. Because of their low solubility, many phytochemicals are poorly absorbed by human body thereby reducing the bioavailability of the phytochemical and this curtails the efficacy of the natural product.

To improve the efficacy of these agents, researchers and manufacturers have begun adopting novel formulation technologies to enhance their bioavailability and in turn increasing their efficacy. There are also efforts from the researchers to have controlled release formulations, which can lead to better dosing compliance.

In this respect, researchers have attempted to combine the phytochemicals with phospholipids to enhance their bioavailability. One such attempt has been made by inventors of Chinese Abandoned Patent Application No CN1657040 (CN '040) and US Patent Publication No US20090131373 (US '373).

The CN '040 Patent Application relates to complex of curcumin or its derivatives and phospholipid and method for making the complex thereof, wherein the curcumin to phospholipid ratio is 1:1 to 1:3. The said complex is assumed to demonstrate enhance bioavailability of the curcumin.

The US20090131373 Patent Publication relates to phospholipids complexes of curcumin or extracts containing it demonstrating improved bioavailability and a process for production of said curcumin-phospholipid complex. The process, as disclosed in US '373, comprises of reacting hydroalcoholic extract of turmeric rhizomes with phospholipids in an alcoholic solvent.

In both, CN '040 and US '373, although the bioavailability is increased, the sustained release of the Curcumin from the complex is questionable. Further, the stability of the Curcumin is questionable since the Curcumin could degrade during the reaction. Additionally, in both the processes, organic solvents were used, which may render the product unsafe for human consumption, if the residues are left behind in the product.

Curcumin-metal oxide complex has been discussed in CN1438225. The major drawback of this invention is the stability of the curcumin during the complexation reaction. It has now been found, by the inventors, that Curcumin undergoes degradation in alkaline conditions. Further, it has now been proved that it is not possible to obtain the high solubility with only metal oxide and curcumin complex.

Further none of the prior arts available in this field have been able to achieve a sustained release of the phytochemical.

With a view of overcoming the problems posed by the prior arts the present inventors have developed a novel complex of a natural compound or natural compound containing component embedded in natural resin matrix, which is stable and demonstrates improved bioavailability and additionally accomplishes sustained release of the phytochemical.

OBJECTS OF INVENTION

The main object of invention is to provide a composition for the prevention and treatment of human and animal disease/disorders and for restoring health, comprising a stabilized composition comprising of a natural compound or natural compound containing component or natural compound present in oleoresin, a divalent or trivalent metal ion and a phospholipid/lysophopholipid whereby the composition demonstrates a sustained release of the natural compound and further demonstrates improved bioavailability of the natural compound or natural compound containing component.

The another main object of invention is to provide a composition for the prevention and treatment of human and animal disease/disorders and for restoring health, comprising a composition containing stabilized tri-molecular complex which comprising of a natural compound or natural compound containing component, a divalent or trivalent metal ion and a phospholipid embedded in oleoresin/resin matrix whereby the tri-molecular complex embedded in oleoresin matrix demonstrates a sustained release of the natural compound and further demonstrates improved bioavailability of the natural compound or natural compound containing component.

Another object of the invention is to provide a process for preparation of the tri-molecular complex optionally embedded in oleoresin matrix which demonstrates an improved stability of the natural compound or natural compound containing component and demonstrates a sustained release and improved bioavailability.

SUMMARY OF INVENTION

In accordance with the above objects, the invention provides a novel herbal composition for the prevention and treatment of human and animal diseases/disorders and for restoring health.

In accordance with the above objects, the invention provides a composition for the prevention and treatment of human and animal disease/disorders and for restoring health, comprising a stabilized composition containing a natural compound or a natural compound containing component, a divalent metal ion and a phospholipid embedded in oleoresin matrix whereby the composition demonstrates a sustained release of the natural compound and further demonstrates improved bioavailability of the natural compound or the natural compound containing component.

In accordance with above objects of the invention, the invention provides a stable tri-molecular complex of a natural compound(s) or a natural compound(s) containing component or a natural compound present in oleoresin, a divalent metal ion(s) and a phospholipid(s).

Furthermore, the invention provides the tri-molecular complex which has been stabilized by using an optional organic acid(s) or inorganic acid (s).

The tri-molecular complex of the invention demonstrates a improved bioavailability of the natural compound or natural compound containing component.

The tri-molecular complex embedded in oleoresin matrix of the invention demonstrates a sustained release of the natural compound or natural compound containing component through swelling of oleoresin matrix in aqueous media.

The invention further provides the use of natural compound containing component(s) or extracts such as Oleoresins, Oleogum resins, gum resins, resins, rosins, other solvent extract (s) from plant and animal source for the preparation of composition.

The invention further provides the tri-molecular complex of natural molecules embedded in natural oleoresin matrix.

The invention finally provides a process for preparation of the tri-molecular complex.

DETAILED DESCRIPTION OF INVENTION

Figure 1:
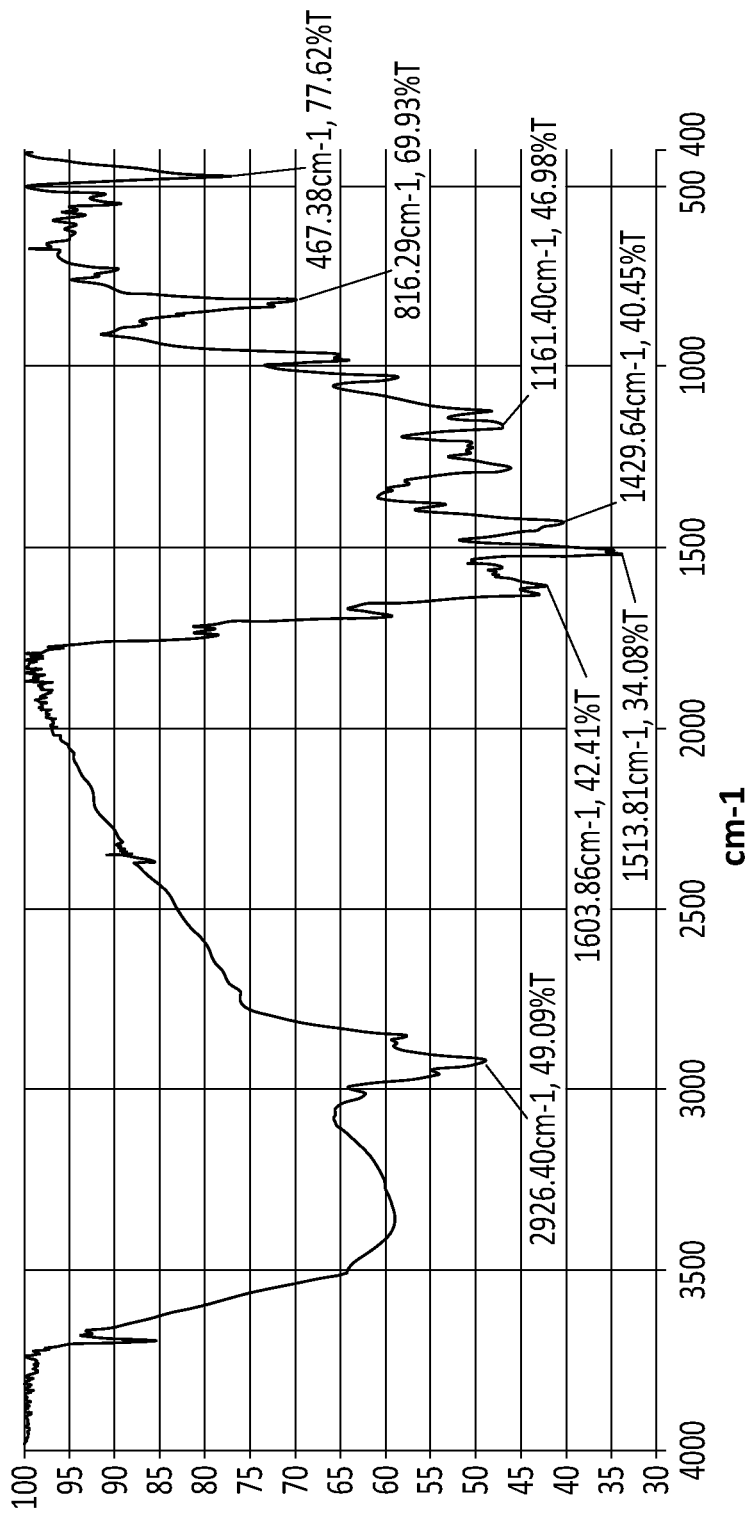
FIG. 1 illustrates the FTIR Spectrum of one embodiment of the invention comprising trimolecular complex of curcumin containing turmeric oleoresin, magnesium ion and phospholipids (from lecithin).
Figure 2:
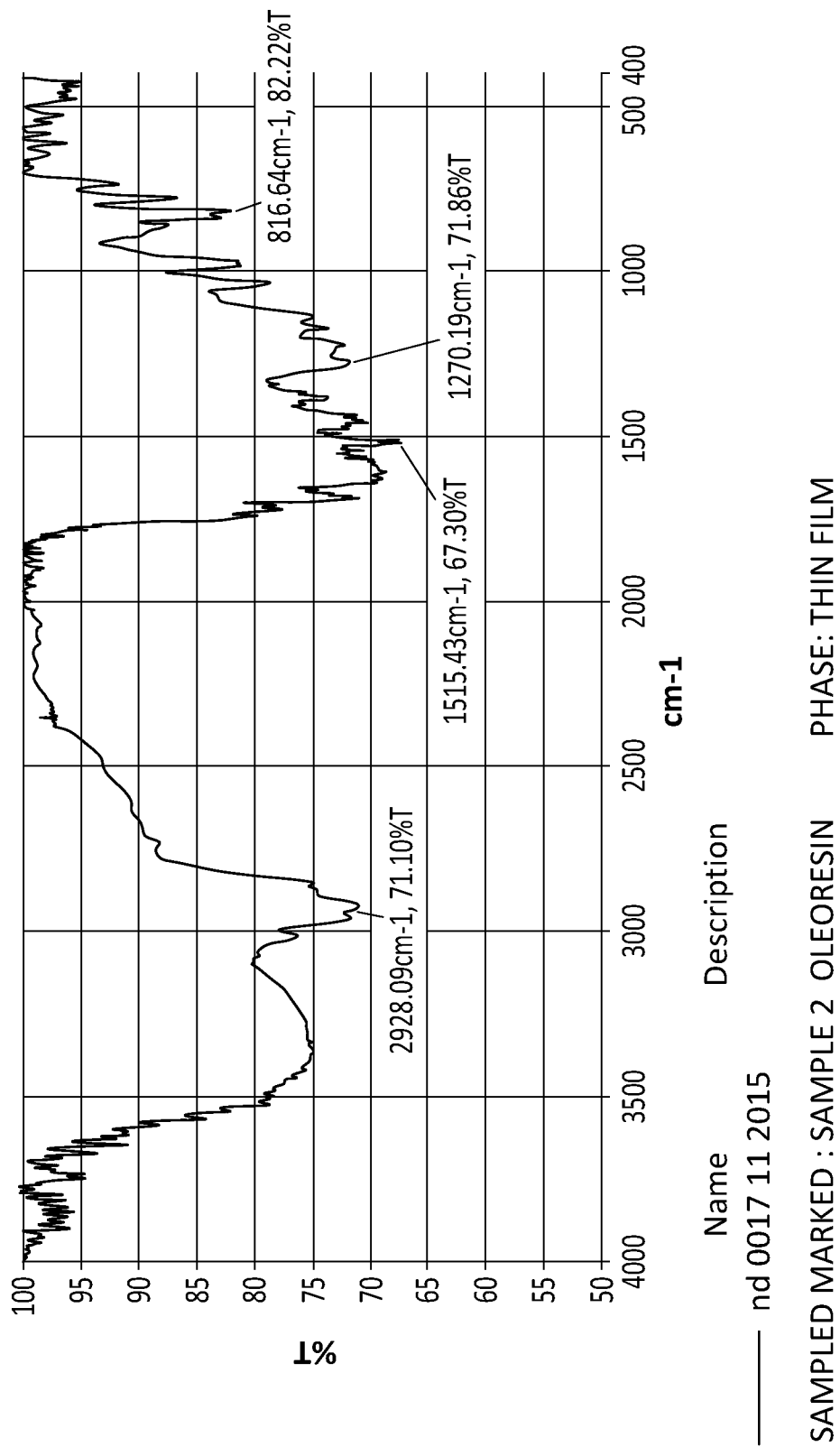
FIGS. 2 to 4 illustrate the FTIR Spectra of the raw materials in accordance with one of the embodiments, namely, turmeric oleoresin, magnesium oxide and Deoiled lecithin.
Figure 3:
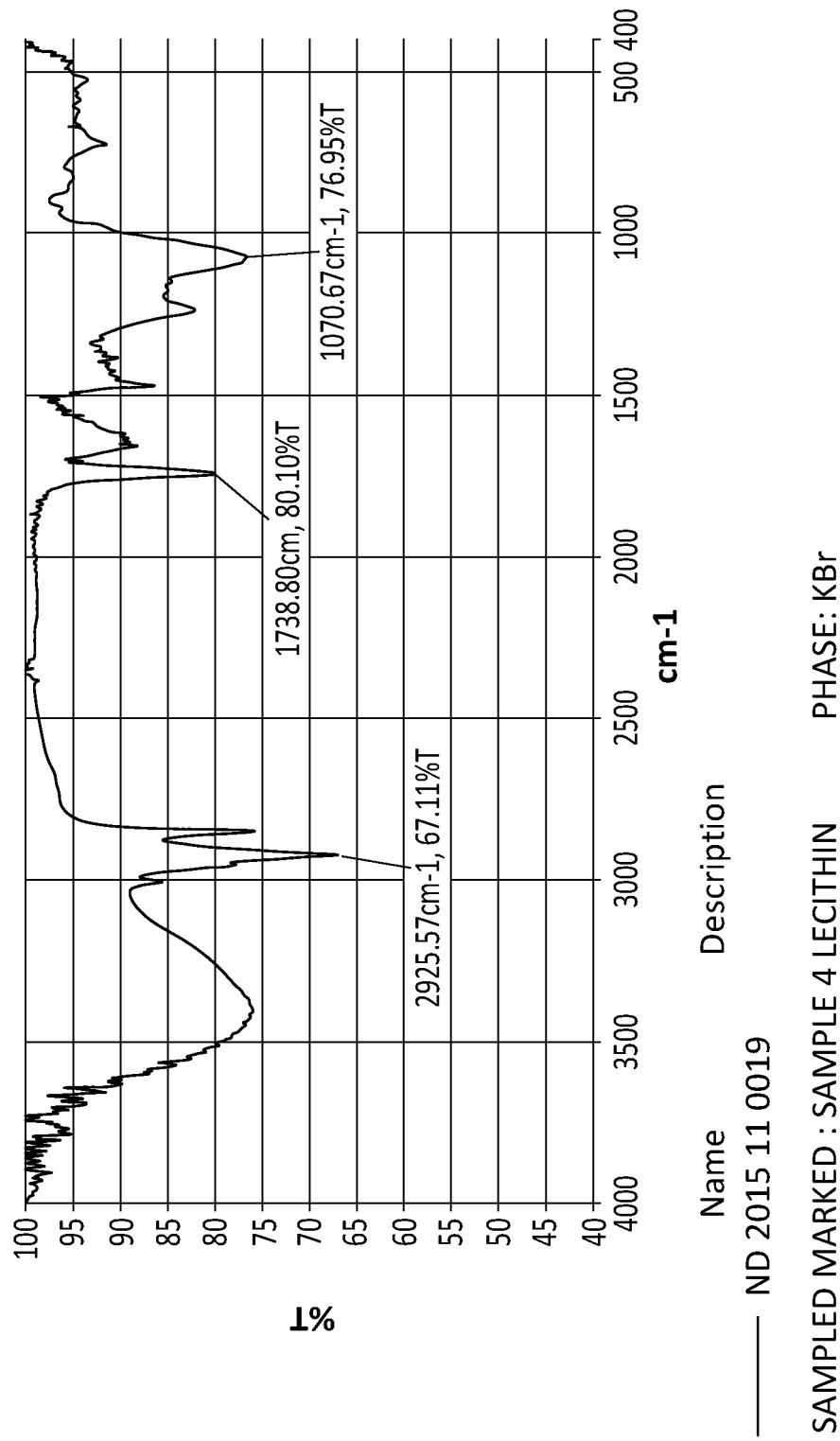
Figure 4:
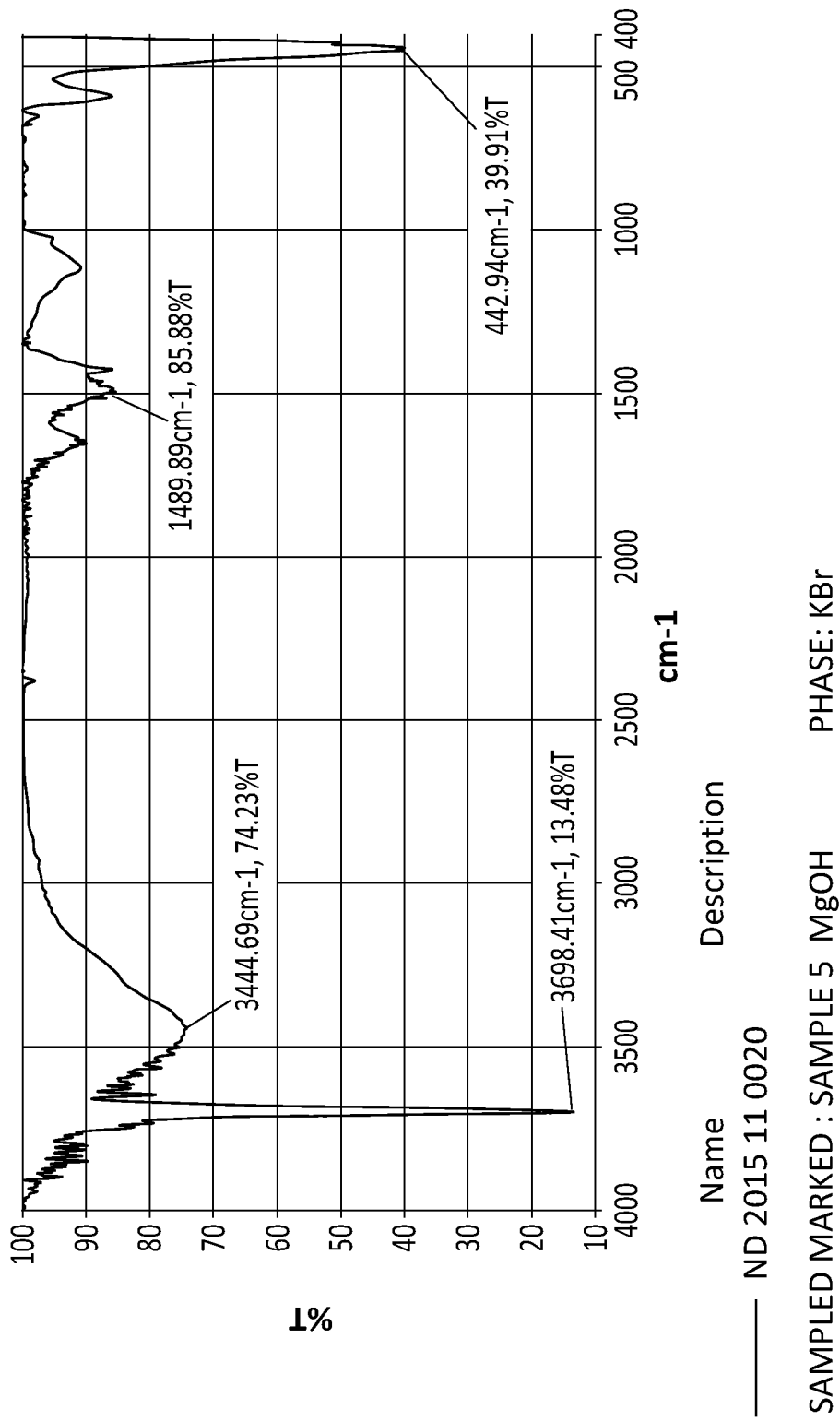

Described herein is a novel herbal composition containing tri-molecular complex. Said tri-molecular complex(s) comprises of a natural compound(s) or a natural compound(s) containing component or a natural compounds containing oleoresin, a divalent metal ion or trivalent metal ion and a phospholipid. The invention further describes a process for preparation of the tri-molecular complex(s) embedded in natural oleoresin matrix.

For the purpose of this invention is the tri-molecular complex as referred in the invention could be used as a medicament, a health supplement, a nutraceutical, a food supplement, beverage supplement, an ayurvedic pharmaceutical and/or a cosmeceutical product for veterinary and/or human application and/or agricultural application.

It has further been found that the tri-molecular complex shows an improved bioavailability. The tri-molecular complex of the invention further demonstrates sustained release effect.

In accordance with the present invention, the general formula I of the tri-molecular complex is as below;

$$P-M^{2+}R \qquad \text{Formula I}$$

Wherein,

P is a natural compound (s), either purified or from natural compound containing component such as plant/animal extracts, Oleoresins, Oleo-gum-resins, gum resins, resins and rosins;

$M^{2+}$ is a divalent or trivalent metal ion; and

R is a phospholipid.

In an embodiment, P may be embedded in an oleoresin matrix.

In an embodiment, P is a natural compound(s) or natural compound(s) containing component.

In subsequent embodiment, P is a natural compound(s) either purified or extract containing the natural compound(s), such as plant/animal extracts, Oleoresins, Oleo-gum-resins, gum resins, resins and rosins.

In yet subsequent embodiment, the natural compound(s) or natural compound(s) containing components P is a phytochemical or phytochemical containing component.

In still subsequent embodiment, the phytochemical or phytochemical containing component P is selected from crude extract, purified extract, fractionated extract, oleoresin, oleo-gum-resin, gum resin, extracts or purified or synthetic phytochemical either from plant or from animal source.

In subsequent embodiment, the phytochemical(s) or phytochemical(s) containing component P is selected from, but not limited to, extract, oleoresin, fractionated extract and purified compounds from *Curcuma longa, Boswellia serrata, Bacopa monnieri,* Marigold, Ginger, *Glycyrrhiza glabra,* Saw palmetto, *Cannabis, Cinnamon* species, *Terminalia chebula, Scutellaria baicalensis, Pinus pinaster* (Maritime pine bark), *Euterpe oleracea* and *Acacia catechu, Silybum marianum, Viscum album, Punica granatum, Camellia sinensis* (Green Tea), Green coffee bean, *Commiphora* (Mukul), *Cassia Fistula, Cannabis, Coleus, Carica papaya, Centella asiatica, Cinnamomum zeylanicum, Cissus quadrangularis, Chlorophytum tuberosum, Curcuma zedoaria, Curcuma xanthorrhiza, Emblica officinalis, Eugenia jambolana, Eurycoma longifolia* Root, *Garcinia cambogia, Garcinia mangostana, Gymnema sylvestre, Indigofera Tinctoria, Momordica charantia* Fruit (Chamomile), *Morinda citrifolia, Moringa oleifera, Mucuna pruriens, Piper nigrum* Fruit, *Phyllanthus niruri, Salacia oblonga, Salacia reticulata, Sphaeranthus indicus, Sida cordifolia, Tagetes erecta* Flower, *Tamarindus indica, Terminalia arjuna, Terminalia chebula, Tribulus terrestris, Trigonella foenum-graecum, Triphala,* Ashwagandha, resverarol, hupericin, Acai, bilberry, Raspberry, Cranberry, grape seed, monagosteen, Noni, Olive, Pomegranate, Beet root.

In another subsequent embodiment, the phytochemical or phytochemical containing component P is a oleoresins, oleo gum resins and gum resins, including spice and herbal/plant oleoresins, wherein said oleoresin, oleo gum resin, gum resin, rosin is selected from, but not limited to, Clove Oleoresins, Curry leaf Oleoresins, Pepper Oleoresins, Cardamom Oleoresins, Chilli Oleoresins, *Capsicum* Oleoresins, Paprika Oleoresins, Ginger Oleoresins, Turmeric Oleoresins, Turmeric oleoresin spent, *Curcuma xanthorrhiza* oleoresin, *Curcuma caesia,* Coriander Oleoresins, Cumin Oleoresins, Celery Oleoresins, Dill Oleoresins, Fenugreek Oleoresins, Garlic Oleoresins, Mace Oleoresins, *Garcinia* Extract, Fennel Oleoresins, Tamarind Oleoresins, *Cinnamon* Oleoresins, Nutmeg Oleoresins, *Cassia* Oleoresins, Galangal Oleoresins, Parsley Oleoresins, Thyme Oleoresins, Marigold Oleoresins, Rosemary Oleoresins, Mustard Oleoresins, Curry Powder Oleoresins, Pine oleoresin, *Curcuma zedoaria* oleoresin, green tea extract, green coffee bran extract, berberin, *Echinacea,* pine bark extract, *Fraxinus excelsior, Cannabis, Coleus forskolii,* Milk Thistle and Vanilla Oleoresins either alone or in combination.

The said oleoresin may contain essential oil, active compounds such as flavonoids, phenolic compounds, terpene, resins, alkaloids, stilbenes, lignins and their metabolites/derivatives, rosins and resins.

The said oleoresin is an extract obtained from all or any of the plant parts such as leaves, root, bark, stem, flower, flower buds, seeds etc.

The said oleoresin is extracted using organic and/or inorganic solvents and hydroalcoholic solvents, selected from, but not limited to, ethyl acetate, ethanol, acetone, hexane, methanol, EDC (ethylene dichloride), carbon dioxide or any other polar or non-polar solvent.

The tri-molecular complex of the invention embeds in a natural resin matrix from the oleoresin or extract or phytochemical containing component. Said natural matrix serves to control the release of natural component P leading to sustained release profile. P contains an active ingredient and a resin. Accordingly, the active ingredient is converted into the tri-molecular complex while, the resin complexes with the metal salts to form a resin metal salt matrix. The tri-molecular complex subsequently embeds in the resin metal salt matrix. The resin metal salt matrix slowly swells in the water, thereby sustaining the release of the tri-molecular complex. The tri-molecular complex, after being released from the resin matrix, form spherical structures which lead to increased bioavailability.

The said trimolecular complex forms spherical and/or cylindrical structures in the presence of water and oil of various sizes.

In another subsequent embodiment, the phytochemical(s) or phytochemical(s) containing component P is an extract from plant, marine source or animal sources such as but not limited to Astaxanthin, Asthaxanthin oleoresin, Krill Oleoresin.

In yet another subsequent embodiment, the phytochemical(s) or phytochemical(s) containing component P is a purified compound selected from, but not limited to, group of flavonoids, phenolic compounds, terpene, resins, alkaloids, stilbenes, lignins, Proanthocyanidins, and their metabolites or derivatives selected from, but not limited to, Curcumin, Boswellic acids, Bacosides, Lutein, Forskolin, Berberin, Ellagic acid, Resveratrol, Catechin, quercitin, Gingerols, caffeine, Pterostilbene, Allicin, Asthaxnathin, Silymarin, Beta-cryptoxanthin, Daidzein, Genistein, hupericin, alkamides, resins, rosins etc.

For the purpose of demonstrating the invention, one preferred natural compound(s) or natural compound containing component P is turmeric oleoresin containing Curcuminoids, essential oil, non-curcuminoid components such as resins.

In an embodiment, the amount of phytochemical(s) or phytochemical(s) containing component P present in the composition ranges from 2 to 98%, preferably, 20 to 70%.

In an embodiment, the divalent metal ion $M^{2+}$ is derived from mineral hydroxide or mineral oxides or mineral chlorides or mineral carbonates.

In subsequent embodiment, the divalent metal ion $M^{2+}$ is derived from a divalent or trivalent metal salt selected from, but not limited to, Calcium Hydroxide ($Ca(OH)_2$)/Calcium Oxide, Magnesium hydroxide ($Mg(OH)_2$)/Magnesium Oxide (MgO), Magnesium Chloride ($MgCl_2$), Zinc Hydroxide ($Zn(OH)_2$)/Zinc Oxide (ZnO) and Iron hydroxide ($Fe(OH)_2$)/Iron Oxide (FeO), di-calcium phosphate ($CaHPO_4$), Calcium Chloride ($CaCl_2$))/Calcium carbonate ($CaCO_3$), Magnesium chloride ($MgCl_2$)/Magnesium carbonate ($MgCO_3$), Aluminium Hydroxide ($Al(OH)_3$), Selenium Hydroxide ($Se(OH)_2$)/Selenium Oxide ($SeO_2$) or combinations thereof. The most preferred divalent metal salts are Calcium Hydroxide ($Ca(OH)_2$) and Magnesium Hydroxide ($Mg(OH)_2$) used either alone or in combination.

In a preferred embodiment, the divalent metal ion $M^{2+}$ is calcium hydroxide and magnesium hydroxides. Wherein, calcium hydroxide and magnesium hydroxide are in powder form with the purity ranging from 10 to 99.9%. The concentration of calcium hydroxide and/or magnesium hydroxide in the final composition ranges from 0.01 to 50%.

In an embodiment, the phospholipid R is selected from, but not limited to, soya, marine source, and egg phospholipids. The phospholipid R has purity in the range of 50 to 100%. The concentration of the phospholipid R is in the said composition ranges from 0.1 to 50%.

In additional embodiment, the tri-molecular complex of the invention is stabilized by addition of an acid. Said acid could be an organic acid or an inorganic acid. The organic acid or inorganic acid is selected from, but not limited to, propionic acids, formic acids, acetic acids, citric acid, butyric acids, valeric acids, caproic acids, oxalic acid, lactic acid, malic acid, benzoic acid and carbonic acid, hydrochloric acid, sulphuric acid, phosphoric acid either alone or in combination. Preferably, the organic acid is propionic acid. The concentration of organic acids ranges from 0.001 to 20%, preferably, 0.1 to 6%.

In another embodiment, the weight ratio of phytochemical(s) or phytochemical(s) containing component P and metal hydroxide $M^{2+}$ is ranges from 25:1 to 1:25, preferably 13:1.

In another embodiment, the weight ratio of phytochemical(s) or phytochemical containing component P and organic acid is ranges from 35:1 to 1:25, preferably 21:1.

In another embodiment, the weight ratio of phytochemicals or phytochemical containing component P and phospholipid R ranges from 25:1 to 1:25, preferably 14:1.

In another embodiment, the molar ratio of phytochemicals and metal hydroxide ranges from 1:5 to 5:1, preferably 1:1.9.

In another embodiment, the molar ratio of phytochemicals and organic acid ranges from 1:5 to 5:1, preferably 1:1.1.

In another embodiment, the resin content in the oleoresin, oleo-gum resin, gum resin or resin is in the range of 0 to 90%.

In another embodiment, the composition contains pharmaceutically or nutraceutically acceptable and food approved excipients such as wetting agents, dispersing agents, glidents, flow property enhancers, preservatives, stabilizer, anti-oxidants, pH modifiers etc.

In an embodiment, the invention provides a process for manufacturing the tri-molecular complex of the invention. Said process for manufacturing the tri-molecular complex comprises of following steps:
(a) Taking measured amount for natural compound(s) or natural compound(s) containing component P in a reaction vessel or a mixer;
(b) optionally heating the natural compounds or natural compound containing component in vessel to suitable temperature;
(c) Optionally, adding organic acid to the natural compound or natural compound containing component P of step (a) and mixing the reaction mixture for 5 minutes;
(d) adding metal hydroxide/oxides $M^{2+}$ to the solution of step (c) and mixing the reaction mixture for 2 to 5 minutes;
(e) adding phospholipid R to reaction mixtures of step (d) and mixing the same for 5 minutes to get semisolid/solid mass;
(f) taking out the semisolid/solid formed in step (e) from the reaction vessel and allowing it to become hard mass/hard cake;
(g) grinding the hard cake of step (f) to a free flowing powder, and
(h) mixing with the optional excipients to form a free flowing powder.

In an alternative embodiment of the process, the phospholipid R can be added before addition of the metal hydroxide or oxide.

In an embodiment wherein P is embedded in an oleoresin matrix, the process for manufacturing the tri-molecular complex in accordance with this embodiment comprises following steps:
1. A process for manufacturing a tri-molecular complex in accordance with claim 2, wherein the process comprises of:
    (a) charging measured amount for natural compound(s) P in the reaction vessel/mixer;
    (b) optionally, heating the natural compounds or natural compound containing component in vessel to suitable temperature;
    (c) adding organic or inorganic acid to the natural compound or natural compound containing component P of step (a) and mixing the reaction mixture for 5 minutes;
    (d) adding $M^{2+}$ to the solution of step (c) and mixing the reaction mixture for 2 to 5 minutes;
    (e) adding phospholipid R to reaction mixtures of step (d) and mixing the same for 5 minutes to become semisolid;
    (f) taking out the semisolid mass formed in step (e) from the vessel and allowing it to become hard cake or hard mass;
    (g) grinding the hard cake of step (f) to a free flowing powder;
    (h) mixing with the optional excipients to form a free flowing powder, and
    (i) preparation into different dosage.

In an advantageous embodiment, the tri-molecular complex of the invention demonstrates improved bioavailability, higher efficiency of crossing blood brain barrier and retinal barrier.

In another advantageous embodiment, the tri-molecular complex of the invention gets embedded in resin/resinate matrix of the natural compound containing component during the process.

In another advantageous embodiment, the tri-molecular complex of the invention delivers higher amount of phytochemical into blood plasma/serum.

In another advantageous embodiment, the tri-molecular complex embedded in resin or resinate matrix of the invention demonstrates a sustained release of the natural compound(s) or phytochemical(s) P for a period of 12 hrs and more in blood plasma/serum.

In additional advantageous embodiment, once the tri-molecular complex is released from the resin matrix, the tri-molecular complex forms spherical particles in aqueous media which lead to enhanced bioavailability of the phytochemical.

In yet another advantageous embodiment, the tri-molecular complex can be used as nutraceutical, dietary supplement, food and beverages, food supplement, beverage supplement, agrifoods supplement/additive, pharmaceutical, an ayurvedic pharmaceutical and/or a cosmeceutical product for plants, veterinary and/or human application.

In yet another advantageous embodiment, the said compositions can be used for the prevention and treatment of inflammatory diseases, reactive oxygen species disease, cognitive diseases, autoimmune diseases, age related diseases, joint related disease, sports injury, down regulating pro-inflammatory cytokines, nuclear factors, all types of cancers, eye diseases, skin disease, oral diseases, infections, all type of pain conditions, weight disorders, cholesterol reducing agent, bile acid sequestering, lipid lowing agent, neurological diseases, oxidation diseases, nutritional disorders, mineral deficiency, dehydration (due to diarrhoea, vomiting, exercise and sports activity), blood disease, liver diseases and respiratory diseases.

In yet another advantageous embodiment, the said product(s) can be used for fortifying beverages with phytochemicals and one such advantage is fortifying tea/coffee with phytochemicals in tea/coffee bags.

In one of the exemplary embodiments, the tri-molecular complex of the invention comprises of a turmeric oleoresin as the natural compound containing component wherein natural compound is curcumin and/or curcuminoids, Magnesium hydroxide as a divalent metal hydroxide and Deoiled lecithin as the phospholipid. The said exemplary embodiment is being stabilized by using propionic acid as the organic acid.

In one of the exemplary embodiments, the tri-molecular complex of the invention comprises of a Ginger oleoresin as the natural compound containing component wherein natural compound is gingerol and/or gingerols, Calcium hydroxide as a divalent metal hydroxide and Deoiled lecithin as the phospholipid. The said exemplary embodiment is being stabilized by using propionic acid as the organic acid.

Example 1

A. Preparation of Turmeric Oleoresin Product:

TABLE 1

Product Composition:

| Sl. No. | Ingredients | Composition (in gm) |
| --- | --- | --- |
| 1 | Turmeric Oleoresin | 82.7 |
| 2 | Propionic acid | 4.0 |
| 3 | Magnesium Hydroxide | 6.4 |
| 4 | Deoiled Lecithin | 5.9 |
| 5 | Precipitated silica | 1.0 |
| Total | | 100.0 |

The structure of the curcumin-magnesium-lecithin tri-molecular complex is as shown in Formula-II and/or Formula III.

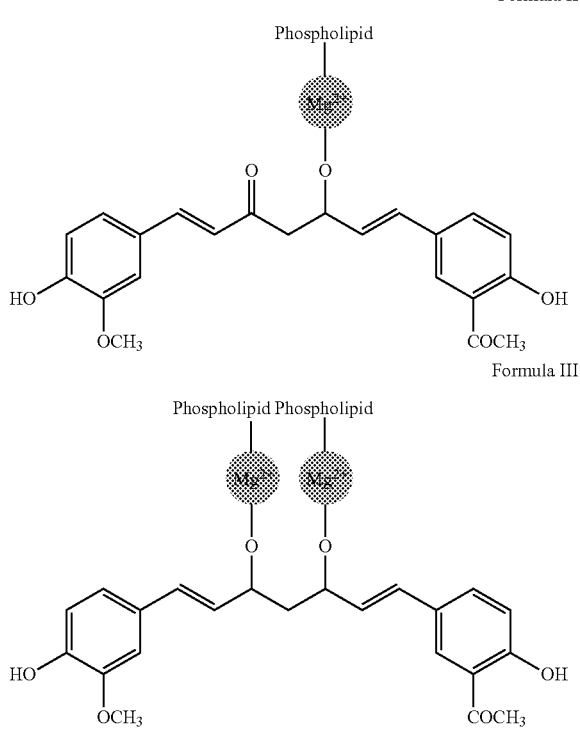

Formula II

Formula III

B. Process for the Preparation of Turmeric Oleoresin Product:
  a. Taking a measured amount of Turmeric oleoresin in the reaction vessel fitted with stirrer or in mixer;
  b. adding propionic acid in to reaction vessel containing turmeric oleoresin of step (a) and mixing the reaction mixture for 3 minutes;
  c. adding Deoiled lecithin powder, to molten reaction mixtures of step (b) and mixing the same for 3 minutes;
  d. adding magnesium hydroxide to the reaction mixture of step (c) and mixing for 8 to 9 minutes; reaction mixture becomes semisolid;
  e. transferring the product from step (d) on to a butter paper (alternatively any vessel of flat surface such as metal trays);
  f. spreading the product of step (e) as thin layer and allowing it to become hard mass (takes 2 to 3 hours to become hard mass);
  g. grounding the hard mass from the step (e) into a fine powder
  h. Optionally adding approved excipients
  i. storing the free flowing powder of step (g) in an air tight container.

The final product is a free flowing powder. Alternatively Deoiled lecithin can be added after adding metal hydroxide. The drying period can be adjusted by adjusting the quantity of metal hydroxide.

C. Analytical Results of Turmeric Oleoresin Product:

The turmeric oleoresin product from example 1 was analysed for total curcuminoids content using standardised HPLC method. The result was;
  1. Percentage of Curcuminoids=37.09%.
  2. Percentage of Curcuminoids=26.23%.

Example 2

Abbreviations Used:
OLNP-08 or Curene:
  Turmeric oleoresin formulation, containing a trimolecular complex comprising Curcumin, Magnesium and phospholipids according to Example 1.
CP01(M):
  Phospholipid complex of curcumin.
  Curcuminoids 95%: standard turmeric extract.
Pharmacokinetic Study in Animals:

The Pharmacokinetics of OLNP-08 (Group I) in comparison with Curcuminoids—95% (Group II) and CP01(M) (Group III) following single oral administration (500 mg/Kg BW; equivalent to Curcuminoids) was carried out in male Wistar Rats. Following dose administration, blood was collected in pre labeled $K_2$EDTA anticoagulant tubes from each animal at 0.00, 1.00, 2.00, 3.00, 4.00, 6.00, 8.00, 10.00, 12.00, 16.00, 18.00 and 24.00 hours. Plasma was separated in pre-labeled vials after centrifugation at 3000 RPM for 10 mins at 4° C. and stored at −70° C. until the bioanalysis. A partially validated LC-MS/MS method was used to quantify Curcumin in $K_2$EDTA Rat plasma over the concentration range of 3.0560 to 1010.6120 ng/mL.

None of the rats exhibited any signs of toxicity during the experimental period. No mortality or morbidity was observed during the experimental period.

Figure 5:
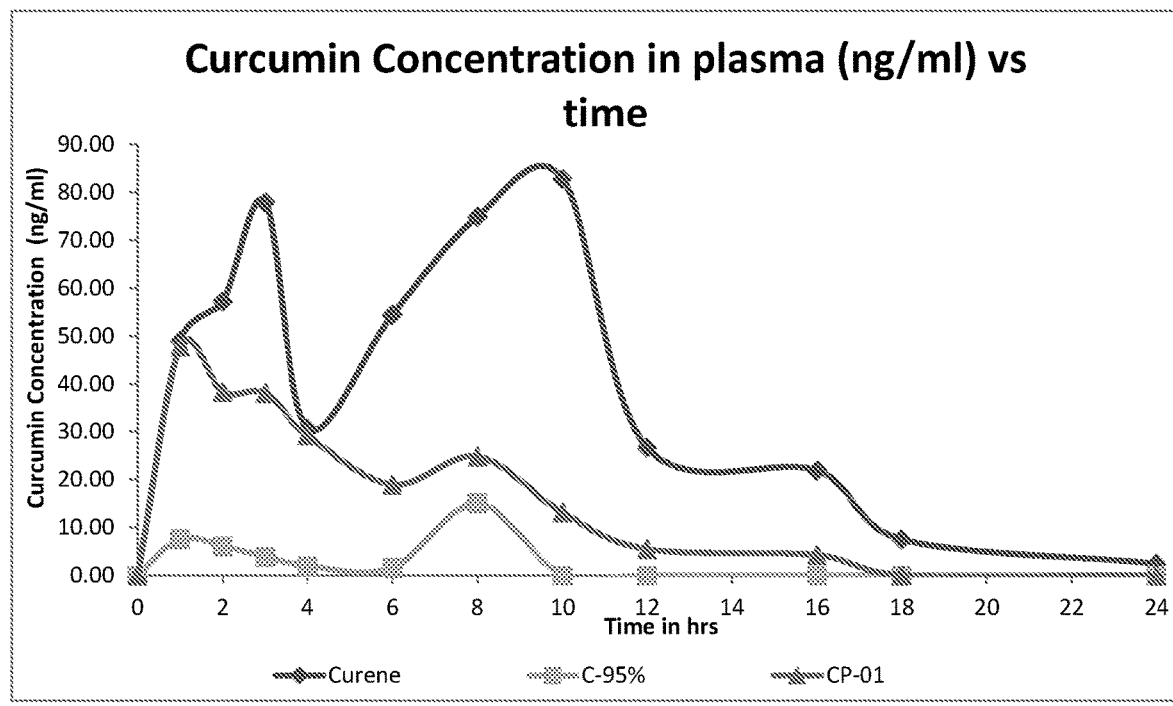
FIG. 5 is a plot illustrating the comparative bioavailability of three formulation namely, formulation according to present invention labelled as OLNP-08 or Curene, phospholipid curcumin complex labelled as CP01(M) and 95% Curcuminoid solution labelled as (C-95%).

The study findings revealed that bioavailability of Curcumin from the test item (OLNP-08) was increased significantly compared with that of reference formulations, Curcuminoids—95% and CP01(M). OLNP-08 was found to have 22.5 and 2.6 times higher $AUC_{0-t}$, and 3.9 and 1.8 times higher $C_{max}$ when compared to Curcuminoids—95% and CP01(M) respectively. It also showed sustained release profile for Curcumin over a period of 24 hrs. Under this experimental conditions, OLNP-08 was found to be superior to Curcuminoids—95% and CP01(M) in increasing the bioavailability and sustained release profile of Curcumin in male Wister Rats. The plot of comparative bioavailability is illustrated in FIG. 5.

Example 3

Brain Transport Study in Animals:

Ability of transporting Curcuminoids into brain by crossing Blood brain barrier by OLNP-08 in comparison with Curcuminoids—95% following single oral administration (500 mg/Kg BW; equivalent to Curcuminoids) was carried out in male Wistar Rats. Three hours after dose administration, animals were euthanized and brain samples were collected from animals from each group. Tissue sections were prepared, fixed and stained with DAPI ((4',6-diamidino-2-phenylindole)). Processed tissue samples were subjected to confocal microscopic studies. All procedures such as dose formulation preparation, dosing, brain collection and tissue processing were performed under monochromatic light.

Figure 6A:
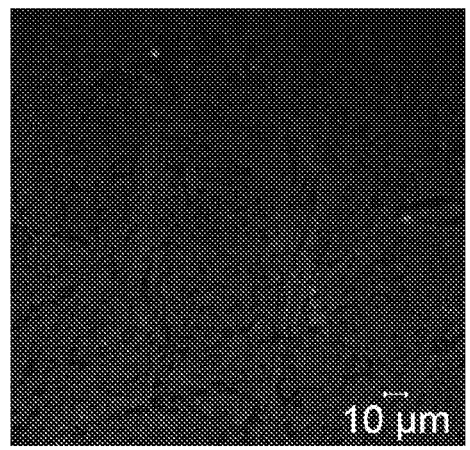
FIGS. 6A and 6B are confocal micrographs illustrating the brain transport study in accordance with Example 3. Single dose of OLNP-08 was administered to one group and 95% Cucuminoid solution was administered to other group. After euthanizing the animals their brain samples were collected and stained with DAPI (4',6-diamidino-2-phenylindole) and observed by confocal microscopy.
Figure 6B:
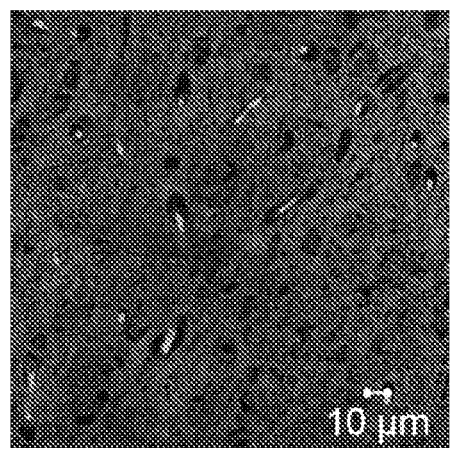

The study findings revealed that significant increase in transport of Curcumin into brain in OLNP-08 treatment group compared with that of reference formulation—Curcuminoids—95%. This was evident by increase in presence of auto-fluorescing Curcuminoids (Green fluorescence) in brain tissues of animals dosed with OLNP-08 when compared to curcunimoids-95% treatment group animals. Under these experimental conditions, OLNP-08 was found superior to Curcuminoids—95% in increasing the bioavailability and transport of Curcumin into brain in male Wister Rats. The results of above study are illustrated in FIGS. 6A and 6B.

Example 4: Super Imagining Study

Figure 7A:
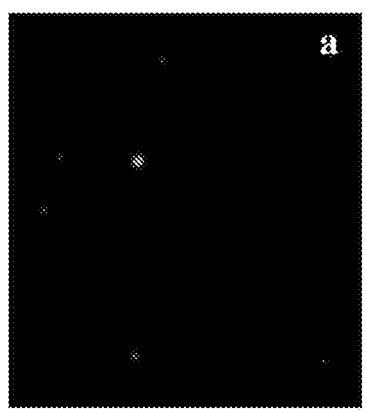
FIGS. 7A, 7B and 7C are confocal micrographs super imaging illustrating the formation of curcumin-magnesium-phospholipid complex. The illustrated image FIG. 7A demonstrates auto-fluorescing green coloured curcumin dots, while FIG. 7B demonstrates blue coloured auto-fluorescing magnesium dots. When both the slides are superimposed cyan coloured spherical dots, as seen in FIG. 7C, are observed at the exact same location as the curcumin and magnesium dots were observed earlier, which confirms that complex formation has taken place. Formation of spherical structure is due to phospholipids.
Figure 7B:
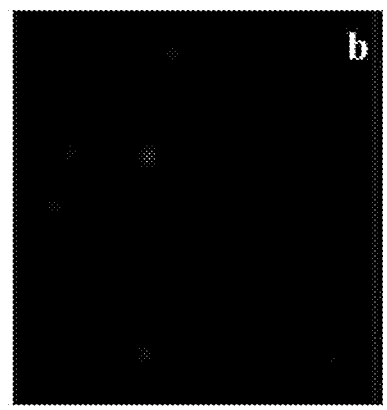
Figure 7C:
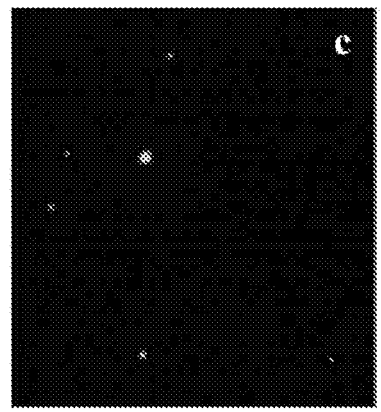

The tri-molecular complex of the invention forms Aqueosomes™ in water and thus making Curcuminoids better soluble and bioavailable. Since Curcumin and magnesium (bound) used in OLNP-08 is auto-fluorescing agents, super imaging confocal microscopic studies were performed to visualize Aqueosomes® and affirm the complex formation. OLNP-08 was added to water, dissolved and observed in super-imaging confocal microscope for presence of Aqueosomes® containing Curcumin-Magnesium complex. Super imaging showed presence of flurosceing spherical structures in water, confirming the formation of Aqueosomes® (FIG. 7C). It also clearly affirms the complex formation of curcumin and magnesium as evident by the presence of superimposing green (Curcumin) (FIG. 7A) and blue (magnesium) fluorescence (FIG. 7B), in each and every Aqueosomex® structures observed. Thus this study clearly confirms the formation of spherical Aqueosome® by OLNP-08 in water and presence of complex between Curcumin, Magnesium and phospholipids in OLNP-08.

Example 5

Bioavailability Study with OLNP-08 in Human Subjects

Figure 8:
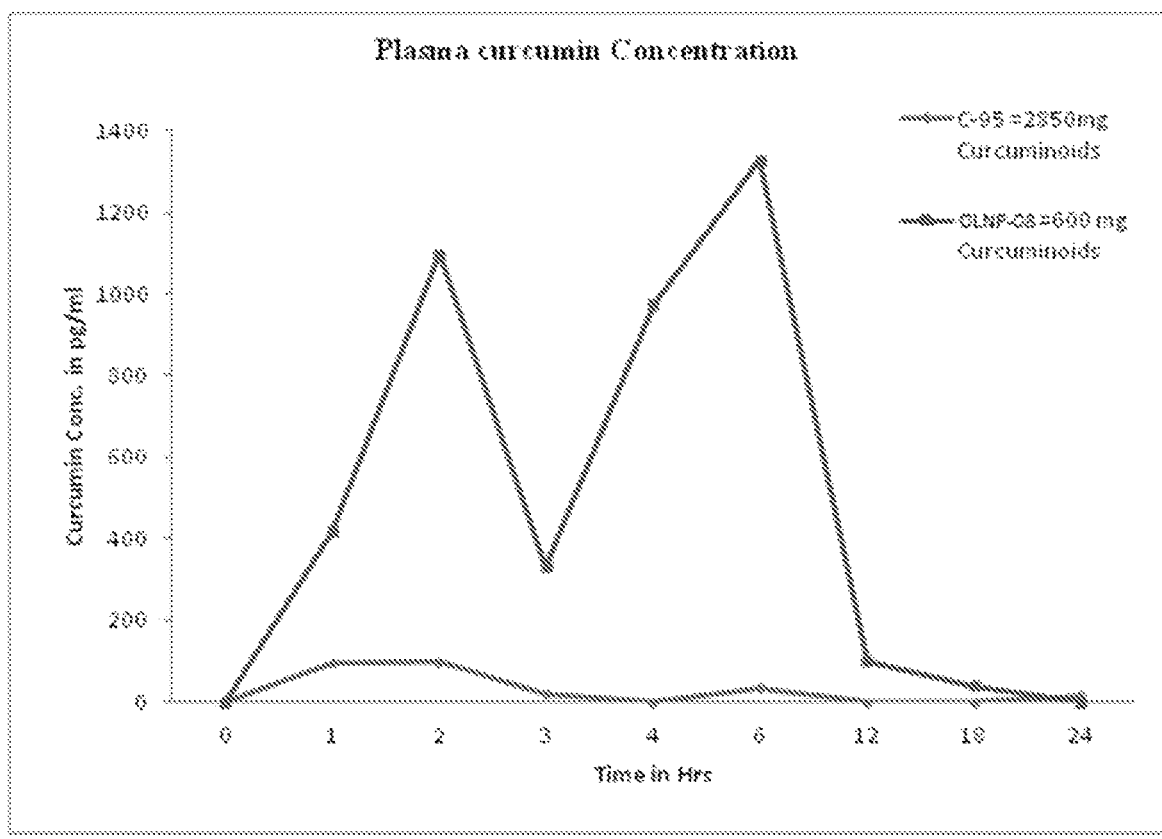
FIG. 8 is a plot exhibiting a comparative bioavailability data in Human subjects for curcuminoids by comparing the bioavialibility of two formulations namely, the formulation of invention labelled as OLNP-08 and 95% curcuminoids labelled as C-95.

An open-label, balanced, randomized, single-dose, two-treatment groups, single-period, parallel, oral comparative bioavailability study with OLNP-08 capsules in comparison with standard Curcuminoids (95%) capsules after a single oral dose administration to healthy adult, human male subjects under fasting conditions was carried out. Two groups comprising 2 subjects each were enrolled for the study. Subjects were administered with 3 gm (500 mg×6 capsules) of OLNP-08 or Curcuminoids—95%. Post-dose blood samples (05 mL each) were collected at: 01.00, 02.00, 03.00, 04.00, 06.00, 08.00, 10.00, 12.00, 14.00, 16.00, 18.00, 20.00 and 24.00 hours and analysed for Curcumin content by LC-MS method. OLNP-08 delivered 128 times more curcumin in human plasma compared to Curcuminoids—95% upon oral administration. As opposed to Curcuminoids—95%, OLNP-08 administration resulted in sustained release of Curcumin in plasma for 24 hours. Thus, OLNP-08 was found to be superior to Curcuminoids—95% in terms of bioavailability and sustained release profile of Curcumin in healthy humans. The results obtained were plotted in graph, which is illustrated in FIG. 8.

Example 6

Figure 9:
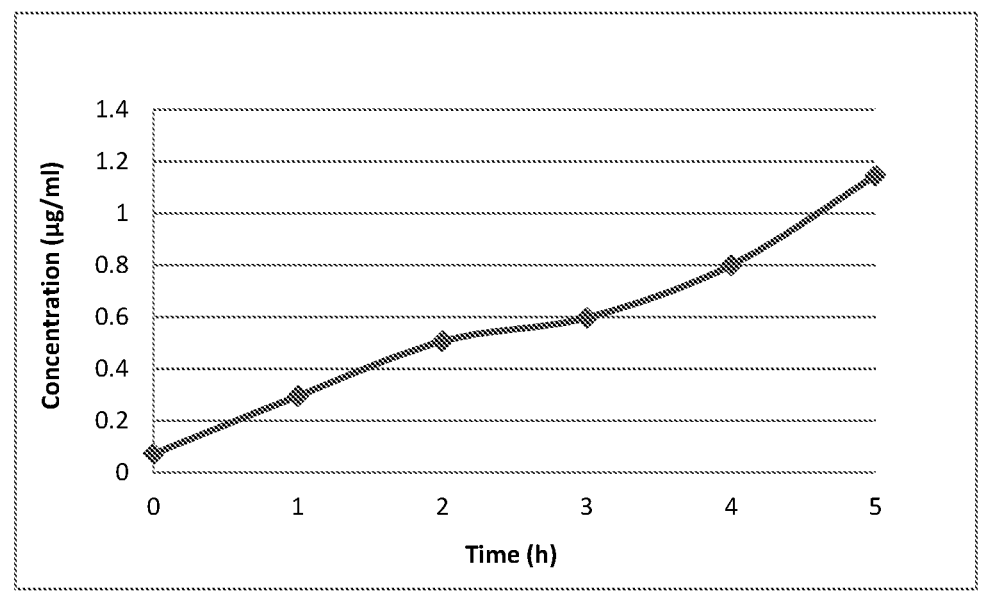
FIG. 9 is a graph illustrating solubility of curcuminoids derived from turmeric oleoresin formulation, labelled as OLNP-08, in an aqueous solution.
Figure 10A:
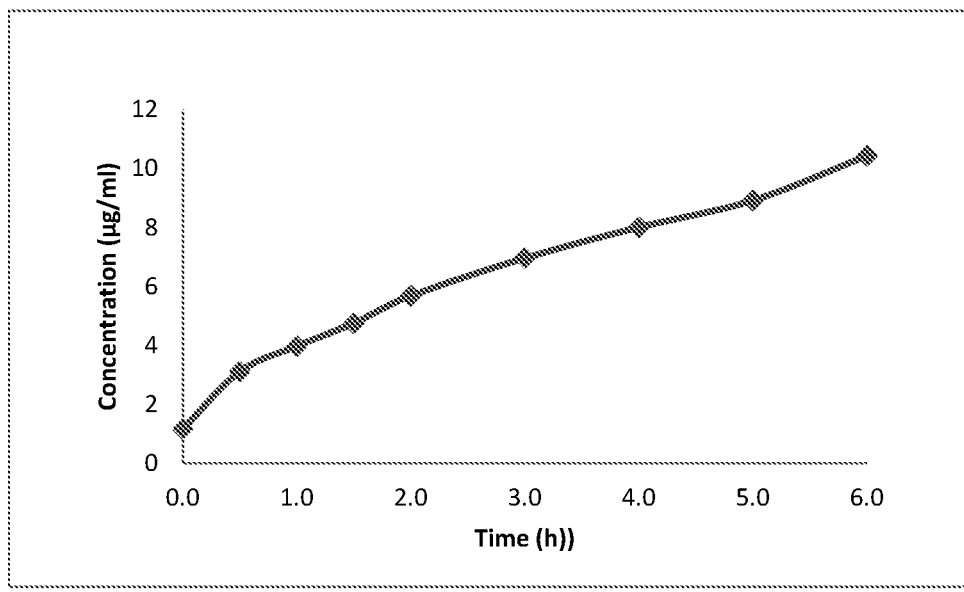
FIGS. 10A and 10B are graphs illustrating the solubility of curcuminoinds in pH1.2 buffer and pH6.8 buffer, respectively.
Figure 10B:
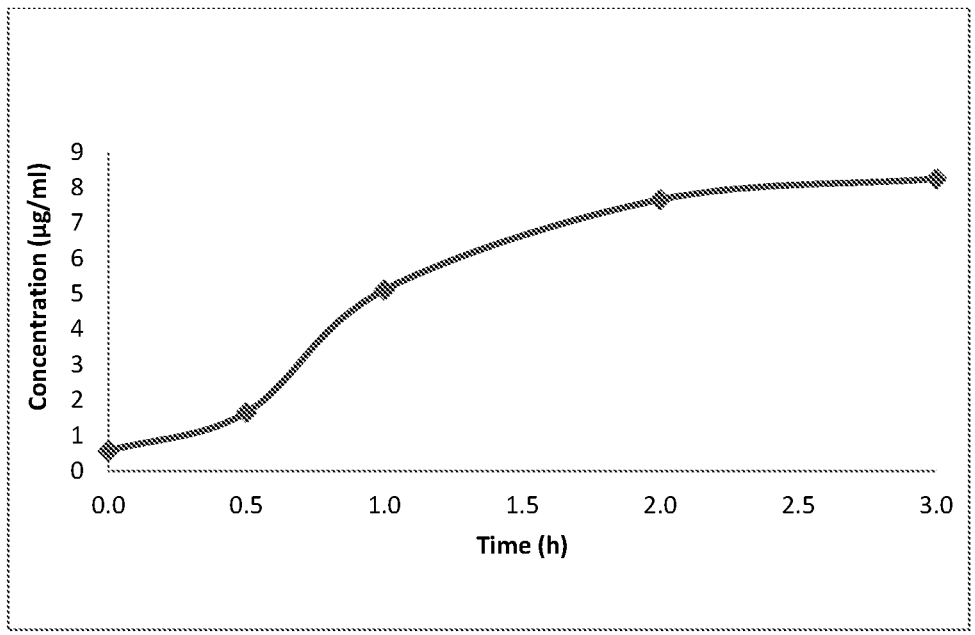
Figure 11:
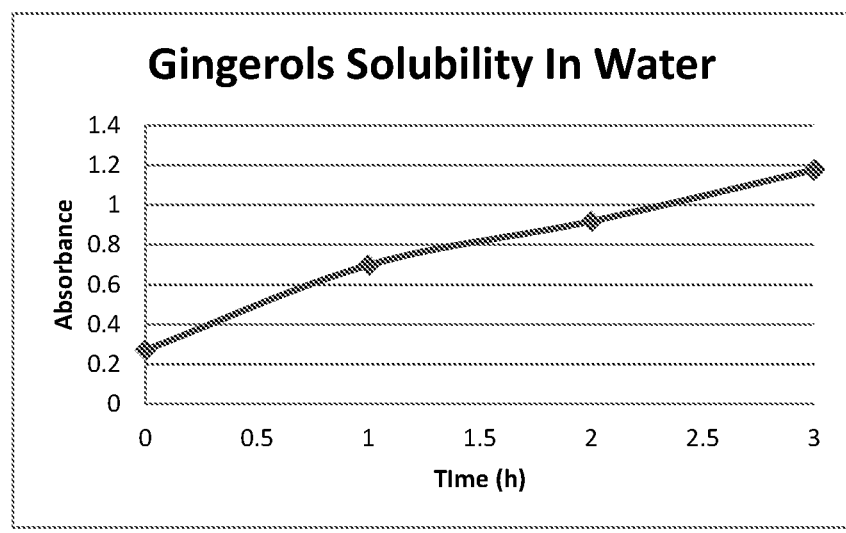
FIG. 11 is a graph illustrating solubility of gingerols derived from OLNP-06 in an aqueous solution.

Solubility of Curcuminoids from OLNP-08 in Water:

Turmeric oleoresin formulation was tested for its solubility in water by dissolving 500 mg of OLNP-08 in 400 ml of water and absorbance at 420 nm was measured using UV-Vis spectrophotometer. Concentration—time graph was plotted. Result (FIG. 6) indicates sustained exponential release of curcuminoids from OLNP-08 in water with time. Concentration-time graph is illustrated in FIG. 9.

Example 7

Composition for preparation of Turmeric oleoresins formulation:

| Sr. No. | Ingredients | Quantity (g) |
| --- | --- | --- |
| 1. | Turmeric Oleoresin | 76.1 |
| 2. | Propionic acid | 4.5 |
| 3. | Hydrochloric acid | 0.5 |
| 4. | Magnesium hydroxide | 6.5 |
| 5. | De-oiled Lecithin | 6.0 |
| 6. | Poly vinyl pyrollidone | 4.5 |
| 7. | Calcium silicate | 1.9 |
| | Total | 100.0 |

Example 8

Composition for preparation of Turmeric oleoresins formulation

| Sr. No. | Ingredients | Quantity (g) |
| --- | --- | --- |
| 1. | Turmeric extract | 81.34 |
| 2. | Propionic acid | 3.92 |
| 3. | Magnesium hydroxide | 6.86 |
| 4. | De-oiled Lecithin | 5.88 |
| 5. | Calcium silicate | 2.0 |
| | Total | 100 |

Example 9

Composition for preparation of Turmeric oleoresin formulation

| Sr. No. | Ingredients | Quantity (g) |
| --- | --- | --- |
| 1. | Turmeric Oleoresin | 76.1 |
| 2. | Propionic acid | 3.0 |
| 3. | Acetic acid | 2.0 |
| 4. | Magnesium hydroxide | 6.5 |
| 5. | De-oiled Lecithin | 6.0 |

Example 10

Composition for preparation of Turmeric oleoresin formulation

| Sr. No. | Ingredients | Quantity (g) |
|---|---|---|
| 6. | Poly vinyl pyrollidone | 4.5 |
| 7. | Calcium silicate | 1.9 |
| | Total | 100.0 |

Example 11

Composition for preparation of Turmeric oleoresin formulation

| Sr. No. | Ingredients | Quantity (g) |
|---|---|---|
| 1. | Turmeric Oleoresin | 74.2 |
| 2. | Propionic acid | 4.0 |
| 3. | Tartaric acid | 2.4 |
| 4. | Magnesium hydroxide | 6.5 |
| 5. | De-oiled Lecithin | 6.0 |
| 6. | Poly vinyl pyrollidone | 5.0 |
| 7. | Calcium silicate | 1.9 |
| | Total | 100 |

Example 12

Composition for preparation of Turmeric oleoresin formulation:

| Sr. No. | Ingredients | Quantity (g) |
|---|---|---|
| 1. | Turmeric oleoresin | 85.0 |
| 2. | Calcium hydroxide | 7.0 |
| 3. | Poly vinyl pyrollidone | 2.5 |
| 4. | De-oiled Lecithin | 5.0 |
| 5. | Calcium silicate | 0.5 |
| | Total | 100.0 |

Composition for preparation of Ginger oleoresin formulation

| Sr. No. | Ingredients | Quantity (g) |
|---|---|---|
| 1. | Ginger oleoresin extract | 81.3 |
| 2. | Poly vinyl pyrollidone | 2.0 |
| 3. | Calcium Hydroxide | 9.8 |
| 4. | De-oiled lecithin | 5.0 |
| 5. | Calcium silicate | 1.90 |
| | Total | 100 |

Example 13

Composition for preparation of Ginger oleoresin formulation

| Sr. No. | Ingredients | Quantity (g) |
|---|---|---|
| 1. | Ginger Oleoresin extract | 73.1 |
| 2. | Propionic acid | 5.0 |
| 3. | Calcium Hydroxide | 10.0 |
| 4. | De-oiled Lecithin | 5.0 |
| 5. | Polyvinyl pyrollidone | 5.0 |
| 6. | Calcium silicate | 1.9 |
| | Total | 100 |

Example 14

Composition for preparation of Marigold oleoresins formulation:

| Sr. No. | Ingredients | Quantity (g) |
|---|---|---|
| 1. | Marigold oleoresin | 74.5 |
| 2. | Propionic acid | 4.0 |
| 3. | Potassium hydroxide | 9.5 |
| 4. | De-oiled Lecithin | 5.0 |
| 5. | Polyvinyl pyrollidone | 5.0 |
| 6. | Calcium silicate | 2.0 |
| | Total | 100.0 |

Figure 12:
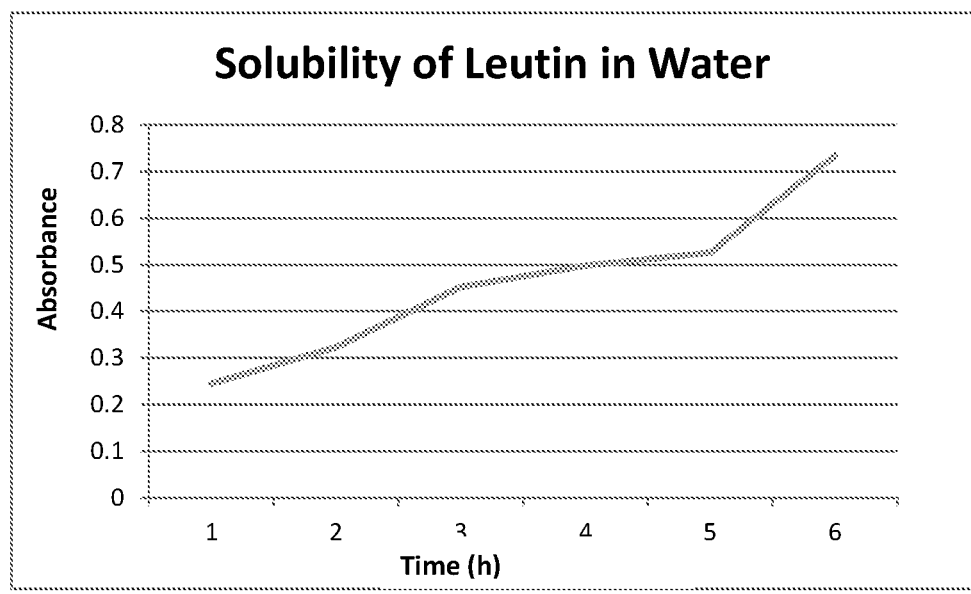
FIG. 12 is a graph illustrating solubility of marigold oleoresin formulation, as lutein, in an aqueous solution.

Marigold oleoresin formulation was tested for its solubility in water by dissolving 500 mg of Marigold oleoresin formulation in water and absorbance was measured at 445 nm using UV-Vis spectrophotometer. Absorbance-time graph (FIG. 12) was plotted. Result indicates sustained exponential release of Lutein in water.

Example 15

Composition for preparation of Marigold oleoresins formulation:

| Sr. No. | Ingredients | Quantity (g) |
|---|---|---|
| 1. | Marigold oleoresin | 75.0 |
| 2. | Adipic acid | 5.0 |
| 3. | Potassium hydroxide | 8.0 |
| 4. | De-oiled Lecithin | 5.0 |
| 5. | Polyvinyl pyrollidone | 5.0 |
| 6. | Calcium silicate | 2.0 |
| | Total | 100.0 |

Example 16

Composition for preparation of Fenugreek oleoresins formulation:

| Sr. No. | Ingredients | Quantity (g) |
|---|---|---|
| 1. | Fenugreek oleoresin | 76.1 |
| 2. | Citric acid | 5.0 |
| 3. | Calcium Hydroxide | 8.0 |
| 4. | De-oiled Lecithin | 5.0 |
| 5. | Poly vinyl pyrollidone | 4.0 |
| 6. | Calcium silicate | 1.9 |
| | Total | 100.0 |

Example 17

Composition for preparation of Cinnamon oleoresin formulation:

| Sr. No. | Ingredients | Quantity (g) |
|---|---|---|
| 1. | Cinnamon oleoresin | 78.1 |
| 2. | Magnesium hydroxide | 8 |
| 3. | Phosphoric acid | 2.2 |
| 4. | De-oiled Lecithin | 4 |
| 5. | Poly vinyl pyrollidone | 5 |
| 6. | Calcium silicate | 1.9 |
|  | Total | 100 |

Example 18

Composition for preparation of Nutmeg oleoresin formulation:

| Sr. No. | Ingredients | Quantity (g) |
|---|---|---|
| 1. | Nutmeg oleoresin | 78.0 |
| 2. | Calcium hydroxide | 7.1 |
| 3. | Citric acid | 4.0 |
| 4. | Deoiled lecithin | 5.0 |
| 5. | Polyvinyl pyrollidone | 5.0 |
| 6. | Calcium silicate | 0.9 |
|  | Total | 100 |

Example 19

Composition for preparation of Paprika oleoresin formulation:

| Sr. No. | Ingredients | Quantity (g) |
|---|---|---|
| 1. | Paprika oleoresin | 80.0 |
| 2. | Magnesium hydroxide | 7.0 |
| 3. | Acetic acid | 4.0 |
| 4. | De-oiled Lecithin | 3.0 |
| 5. | Polyvinylk pyrollidone | 4.0 |
| 6. | Calcium silicate | 2.0 |
|  | Total | 100 |

Example 20

Composition for preparation of *Capsicum* oleoresin formulation:

| Sr. No. | Ingredients | Quantity (g) |
|---|---|---|
| 1. | *Capsicum* oleoresin | 80.4 |
| 2. | Magnesium hydroxide | 9.6 |
| 3. | De-oiled Lecithin (Phospholipids) | 3.7 |
| 4. | Polyvinyl pyrollidone | 4.3 |
| 5. | Calcium silicate | 2.0 |
|  | Total | 100.0 |

Example 21

Composition for preparation of highly concentrated powdered *Coleus forskohlii* oleoresin:

| Sr. No. | Ingredients | Quantity (g) |
|---|---|---|
| 1. | *Coleus Forskohlii* | 77.0 |
| 2. | Magnesium hydroxide | 7.4 |
| 3. | Acetic acid | 3.6 |
| 4. | De-oiled lecithin | 5.0 |
| 5. | Polyvinyl pyrollidone | 5.0 |
| 6. | Calcium silicate | 2.0 |
|  | Total | 100.0 |

Figure 13:
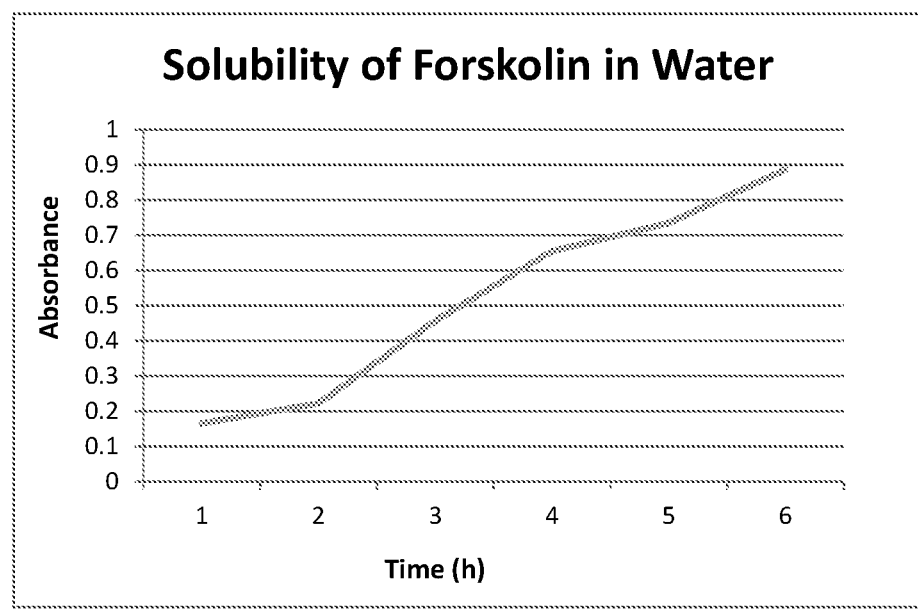
FIG. 13 is a graph illustrating solubility of *Coleus forskohlii* oleoresin, as forskolin, in an aqueous solution.

*Coleus* oleoresin formulation was tested for its solubility in water by dissolving 500 mg of *Coleus* oleoresin formulation in water and absorbance was measured at 210 nm using UV-Vis spectrophotometer. Absorbance-time graph (FIG. 13) was plotted. Result indicates sustained exponential release of Forskolin in water.

Example 22

Composition for preparation of *Boswellia* gum resin formulation:

| Sr. No. | Ingredients | Quantity (g) |
|---|---|---|
| 1. | *Boswellia* gum resin | 75.0 |
| 2. | Magnesium hydroxide | 8.0 |
| 3. | Tartaric acid | 5.0 |
| 4. | De-oiled Lecithin | 5.0 |
| 5. | Polyvinyl pyrollidone | 5.0 |
| 6. | Calcium silicate | 2.0 |
|  | Total | 100.0 |

Figure 14:
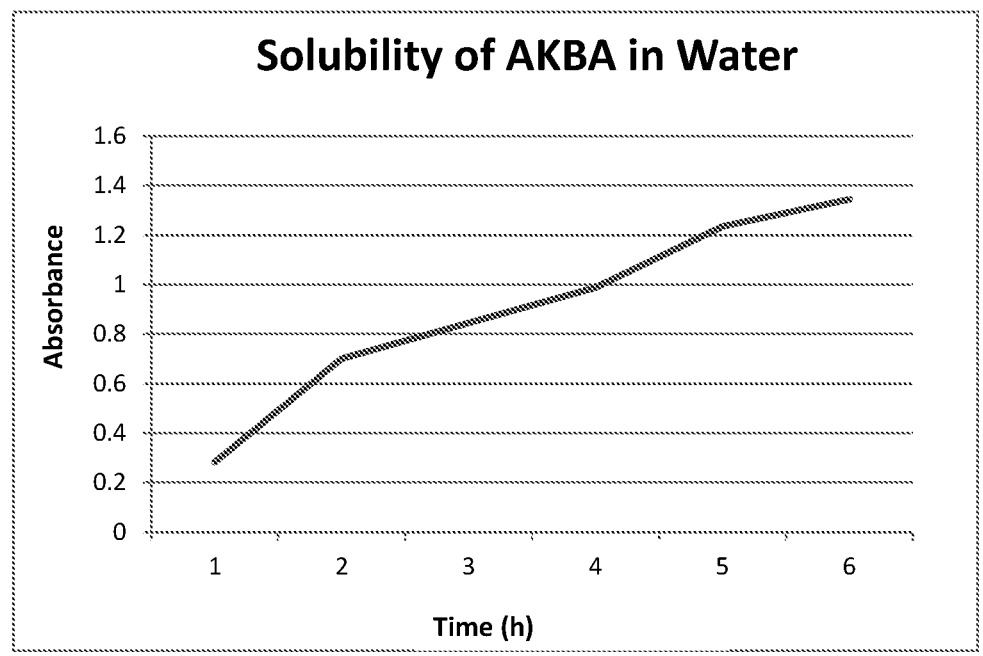
FIG. 14 is a graph illustrating solubility of Bosweilla oleoresin, as AKBA, in an aqueous solution.

*Boswellia* oleoresin formulation was tested for its solubility in water by dissolving 500 mg of *Boswellia* oleoresin formulation in water and absorbance was measured at 254 nm using UV-Vis spectrophotometer. Absorbance-time graph (FIG. 14) was plotted. Result indicates sustained exponential release of AKBA in water.

Example 23

Composition for preparation of Garlic Oleoresin formulation:

| Sr. No. | Ingredients | Quantity (g) |
|---|---|---|
| 1. | Garlic oleoresin | 78.0 |
| 2. | Magnesium hydroxide | 9.0 |
| 3. | Acetic acid | 2.0 |
| 4. | De-oiled Lecithin | 4.0 |
| 5. | Polyvinyl pyrollidone | 5.0 |
| 6. | Calcium silicate | 2.0 |
|  | Total | 100.0 |

Figure 15:
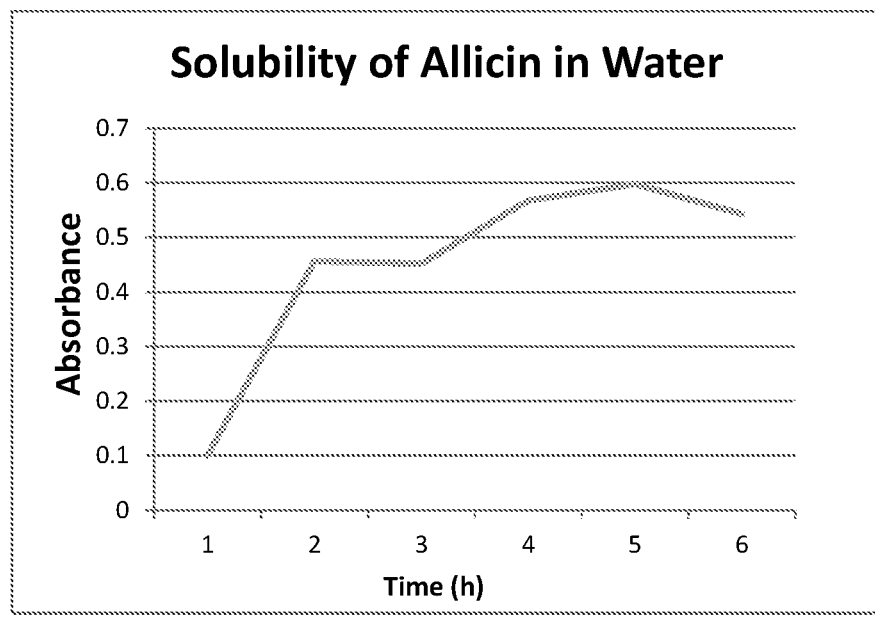
FIG. 15 is a graph illustrating solubility of Garlic oleoresin, as Allicin, in an aqueous solution.
Figure 16:
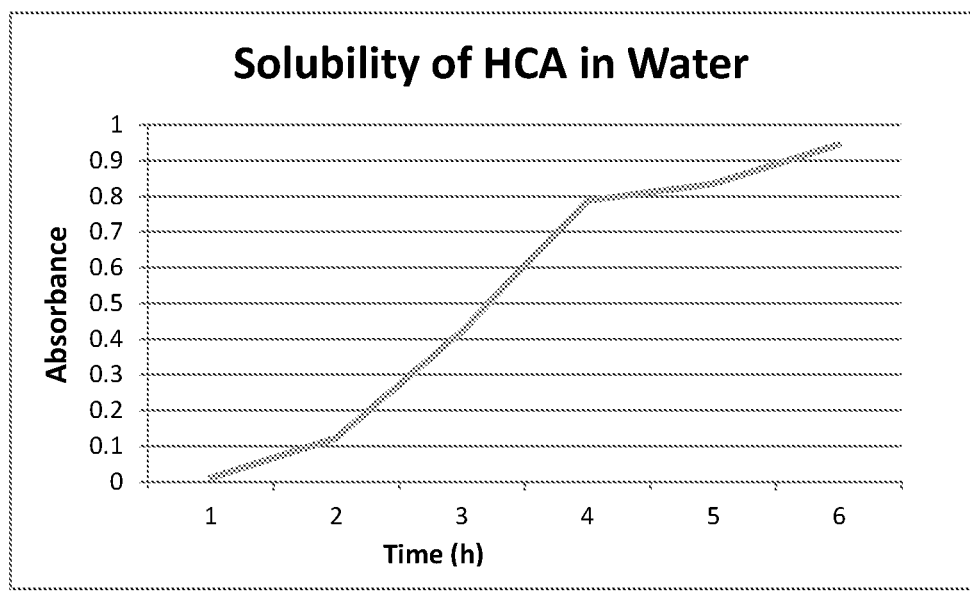
FIG. 16 is a graph illustrating solubility of Garcenia oleoresin, as HCA, in an aqueous solution.

Garlic oleoresin formulation was tested for its solubility in water by dissolving 500 mg of Garlic oleoresin formulation in water and absorbance was measured at 240 nm using UV-Vis spectrophotometer. Absorbance-time graph was plotted (FIG. 15). Result indicates sustained exponential release of Allicin in water.

Example 24

Composition for preparation of Garlic Oleoresin formulation:

| Sr. No. | Ingredients | Quantity (g) |
|---|---|---|
| 1. | Milk Thistle oleoresin | 78.0 |
| 2. | Magnesium hydroxide | 9.0 |
| 3. | Acetic acid | 2.0 |
| 4. | De-oiled lecithin | 4.0 |
| 5. | Polyvinyl pyrollidone | 5.0 |
| 6. | Calcium silicate | 2.0 |
|  | Total | 100.0 |

Example 25

Composition for preparation of Curcuminoids formulation:

| Sr. No. | Ingredients | Quantity (g) |
|---|---|---|
| 1. | Curcuminoids (95%) | 60.0 |
| 2. | Magnesium hydroxide | 9.0 |
| 3. | Propionic acid | 20.0 |
| 4. | De-oiled lecithin | 4.0 |
| 5. | Polyvinyl pyrollidone | 5.0 |
| 6. | Calcium silicate | 2.0 |
|  | Total | 100.0 |

Example 26

Composition for preparation of Lutein formulation:

| Sr. No. | Ingredients | Quantity (g) |
|---|---|---|
| 1. | Lutein (98%) | 60.0 |
| 2. | Magnesium hydroxide | 9.0 |
| 3. | Propionic acid | 20.0 |
| 4. | De-oiled Lecithin | 4.0 |
| 5. | Polyvinyl pyrollidone | 5.0 |
| 6. | Calcium silicate | 2.0 |
|  | Total | 100.0 |

Example 27

Composition for preparation of Berberine formulation:

| Sr. No. | Ingredients | Quantity (g) |
|---|---|---|
| 1. | Berberine (98%) | 78.0 |
| 2. | Magnesium hydroxide | 9.0 |
| 3. | Propionic acid | 2.0 |
| 4. | De-oiled Lecithin | 4.0 |
| 5. | Polyvinyl pyrollidone | 5.0 |
| 6. | Calcium silicate | 2.0 |
|  | Total | 100.0 |

Example 28

Composition for preparation of Forskolin formulation:

| Sr. No. | Ingredients | Quantity (g) |
|---|---|---|
| 1. | Forskolin | 60.0 |
| 2. | Magnesium hydroxide | 9.0 |
| 3. | Propionic acid | 20.0 |
| 4. | De-oiled Lecithin | 4.0 |
| 5. | Polyvinyl pyrrolidone | 5.0 |
| 6. | Calcium silicate | 2.0 |
|  | Total | 100.0 |

Example 29

Composition for preparation of *Garcinia* oleoresin formulation:

| Sr. No. | Ingredients | Quantity (g) |
|---|---|---|
| 1. | *Garcinia* Oleoresin | 70.0 |
| 2. | Magnesium hydroxide | 10.0 |
| 3. | Propionic acid | 6.0 |
| 4. | De-oiled Lecithin | 6.0 |
| 5. | Polyvinyl pyrrolidone | 6.0 |
| 6. | Calcium silicate | 2.0 |
|  | Total | 100.0 |

Solubility Studies of Garcenia Oleoresin:

Garcenia oleoresin formulation was tested for its solubility in water by dissolving 500 mg of Garcenia oleoresin formulation in water and absorbance was measured at 208 nm using UV-Vis spectrophotometer. Absorbance-time graph was plotted. Result indicates sustained exponential release of HCA in water.

We claim:

1. A capsule consisting essentially of Ginger Oleoresin extract, Propionic acid, Calcium Hydroxide, De-oiled Lecithin, Polyvinyl pyrrolidone and Calcium silicate.

2. A sustained release composition consisting essentially of Ginger Oleoresin extract, Propionic acid, Calcium Hydroxide, De-oiled Lecithin, Polyvinyl pyrrolidone and Calcium silicate.

3. The capsule according to claim 1, wherein the ginger oleoresin extract, the calcium hydroxide, and the de-oiled lecithin form a tri-molecular complex of formula I:

$$P\text{-}M^{n+}\text{-}R \qquad \text{Formula I}$$

wherein,
P is the ginger oleoresin extract;
$M^{n+}$ is a calcium ion derived from the calcium hydroxide, wherein n is 2; and
R is the de-oiled lecithin.

4. The sustained release composition according to claim 2, wherein the ginger oleoresin extract, the calcium hydroxide, and the de-oiled lecithin form a tri-molecular complex of formula I:

$$P\text{-}M^{n+}\text{-}R \qquad \text{Formula I}$$

wherein,
P is the ginger oleoresin extract;
$M^{n+}$ is a calcium ion derived from the calcium hydroxide, wherein n is 2; and
R is the de-oiled lecithin.

5. The capsule according to claim 1, wherein a complex is formed by reaction between the ginger oleoresin extract, the calcium hydroxide, and the de-oiled lecithin.

6. The sustained release composition according to claim 2, wherein a complex is formed by reaction between the ginger oleoresin extract, the calcium hydroxide, and the de-oiled lecithin.

* * * * *